United States Patent [19]
Gekhter et al.

[11] Patent Number: 5,800,340
[45] Date of Patent: Sep. 1, 1998

[54] EXTERNAL PENILE SUPPORT DEVICE

[76] Inventors: Vladimir Gekhter, 5105 Mulford Ave.;
Gregory Goldman, 4912 Jarvis, both of Skokie, Ill. 60077

[21] Appl. No.: 706,193
[22] Filed: Aug. 30, 1996
[51] Int. Cl.⁶ .................................................. A61F 5/00
[52] U.S. Cl. ............................................................ 600/39
[58] Field of Search ................................... 600/38–41

[56] References Cited

U.S. PATENT DOCUMENTS

| | | | |
|---|---|---|---|
| 853,410 | 5/1907 | Huebner | 600/39 |
| 4,262,662 | 4/1981 | Allinson | 600/39 |
| 4,653,484 | 3/1987 | Cannon | 600/39 |

FOREIGN PATENT DOCUMENTS

| | | | |
|---|---|---|---|
| 0711544 | 9/1931 | France | 600/39 |
| 1688865 | 11/1991 | U.S.S.R. | 600/41 |
| 1826885 | 7/1993 | U.S.S.R. | 600/39 |
| 0884357 | 12/1961 | United Kingdom | 600/39 |
| 1144083 | 3/1969 | United Kingdom | 600/39 |

*Primary Examiner*—John P. Lacyk
*Attorney, Agent, or Firm*—Paul H. Gallagher

[57] ABSTRACT

A frame made of a single one-piece filament, bent at the middle to form a support loop which fits in the groove inwardly of the glans, support rods lead inwardly from the support loop where they are mounted in a joint, a detachable support ring being swingably mounted in the joint. A retainer is slidably mounted on the support rods which tightens and loosens the support loop, and holds the support rods in spaced position.

12 Claims, 2 Drawing Sheets

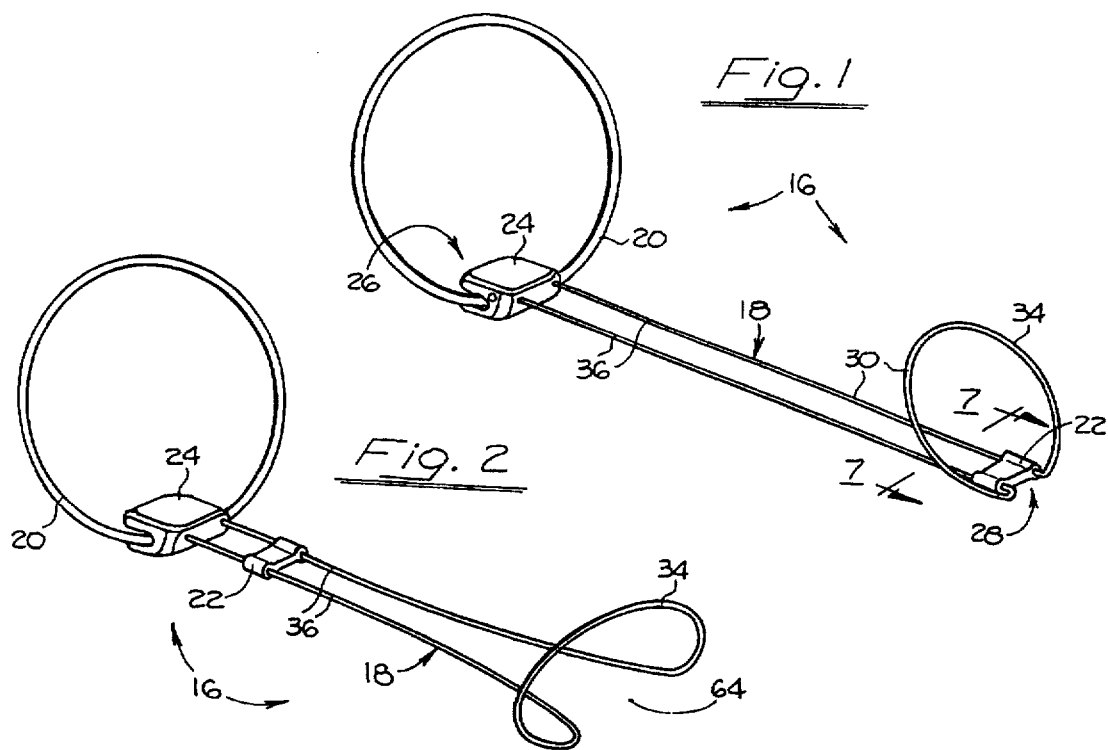
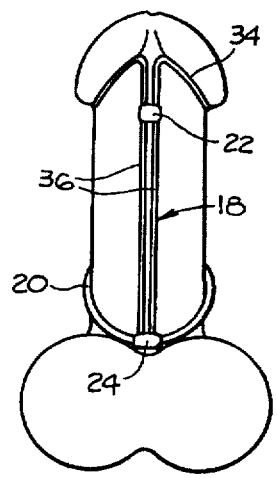
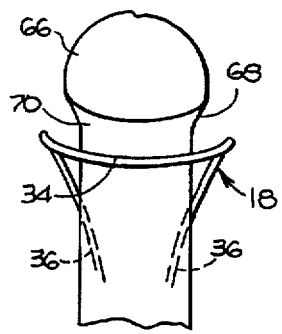
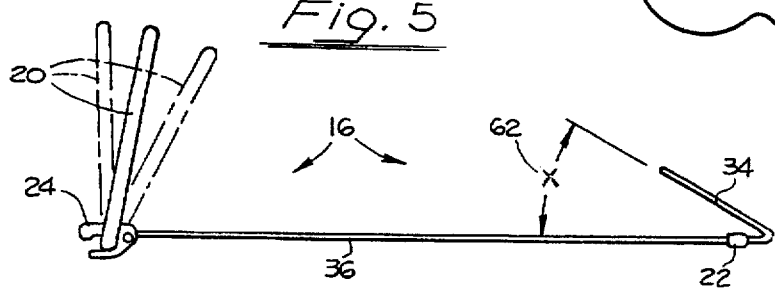

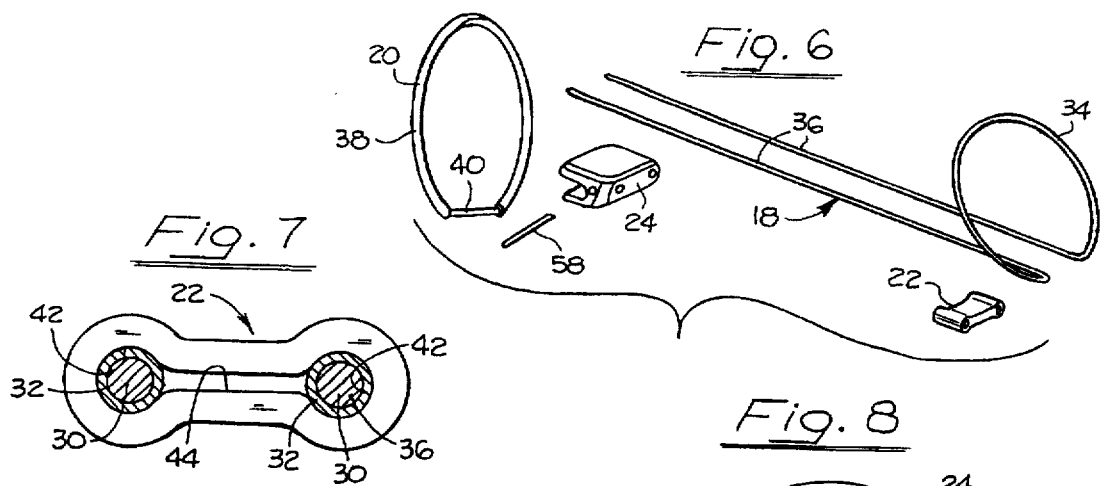
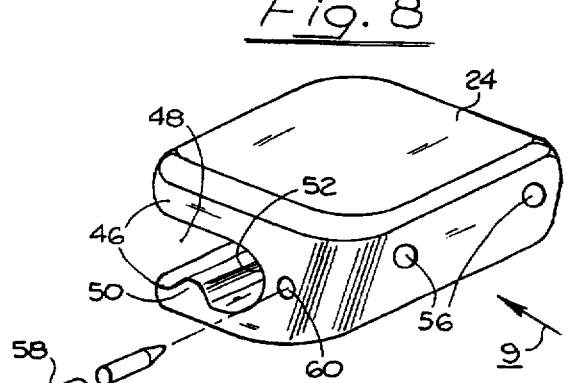
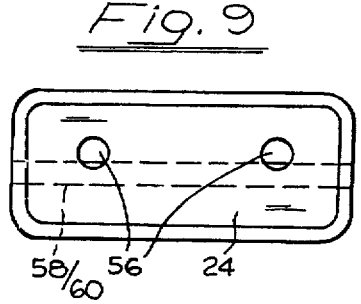
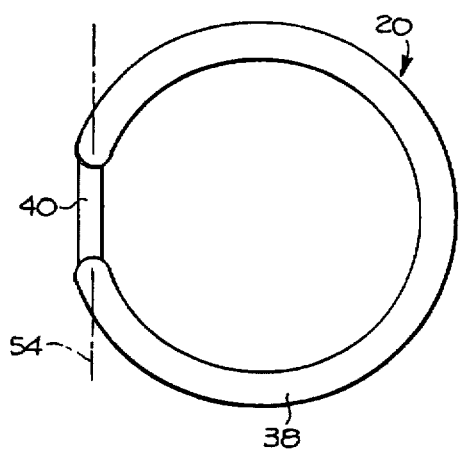
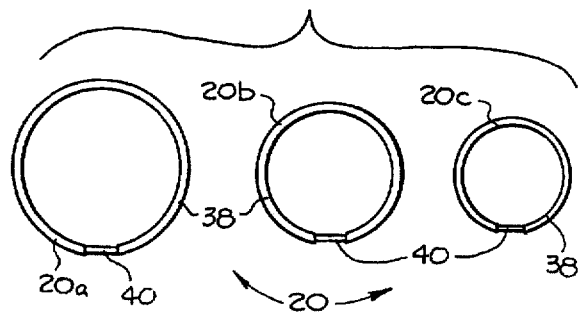

5,800,340

EXTERNAL PENILE SUPPORT DEVICE

FIELD OF THE INVENTION

The invention resides in the field of overcoming impotence in the male. It relates more particularly to an external support device for the penis.

BACKGROUND OF THE INVENTION

A significant number of males are impotent. Their impotence may be physiologically or psychologically induced and is generally manifested by an inability to obtain an erection of the penis. The psychologically related impotency problems are usually curable whereas many of the physiologically related cases are incurable. For example, a prevalent cause of male impotency is diabetes which is generally incurable. In contrast, impotency from other causes, including deficiencies in thyroid functions, reduced arterial flow, the use of drugs and alcohol, anatomical problems and postsurgical manifestations, are generally curable.

The prior art includes many forms of devices and techniques to overcome the problem, including implants, pneumatic, hydraulic and electrical devices, chemical treatment programs, and prostheses.

While the above prior art devices may, in some situations, temporarily relieve the problem, they often cause other problems or are inadequate for prolonged use. For example, implants are known to be seriously ineffective and even dangerous. Likewise the known pneumatic, hydraulic and electric devices are clumsy and inconvenient whereas the chemical treatment program is generally time consuming and yields uncertain results.

Prosthetic devices are worn on the exterior of the penis and are designed to apply pressure to the penis' superficial dorsal vein and corpora cavernosa and further to constrict the flow of blood that would otherwise leave the penis, but flaws of previous prosthesis include:

Protruding elements may push into the fleshy or flaccid part of the penis, missing the superficial dorsal vein, thereby causing great discomfort and interfering with the stimulation and maintenance of an erection.

They slip and objectionably rotate on the penis and prevent it from properly engaging or applying pressure to the superficial dorsal vein.

They generally include a number of parts which often become disassembled during use, resulting in injury to both the user and the user's partner.

They generally are bulky and include individual components with large cross-sections, and often include crevices which provide an environment for bacterial growth.

They are ineffective in retaining their contoured shape and their difficulty in fitting different sized penises. Moreover, they often include corrosive materials and are expensive to manufacture due to their relatively complex designs.

Despite the numerous disadvantages with previous male prostheses, they are still widely used. Thus, while these prostheses may have some limited effectiveness in maintaining an erection for a short period of time they do so in a less than satisfactory manner.

SUMMARY OF THE INVENTION

Accordingly, a main object of the present invention is to provide a male prosthesis that overcomes the foregoing disadvantages.

Other advantages are that the prosthesis:

Effectively and comfortably maintains the penis in a natural erected disposition.

Does not rotate on the penis and therefore reliably applies uniform pressure to the necessary veins in the penis for optimally stimulating and maintaining an erection.

Distributes the tension from the erection over the penis and pubis area.

Does not have areas which may support bacterial growth.

Has a coefficient of friction that is less than that of the penile skin or the skin of the partner.

Is of simple construction, which increases the reliability and durability of the prosthesis, and reduces manufacturing costs.

Will not become disassembled, and thereby it precludes harm to the user and the user's partner.

Includes a frame with components which have a small cross-section.

Will retain its shape during use, and accommodate all erect and non-erect penis sizes without adjustment.

Is made entirely from non-corrosive materials.

PENILE ERECTOR

BRIEF DESCRIPTIONS OF THE FIGURES OF THE DRAWINGS

FIG. 1 is a perspective view of the penile erector of the invention.

FIG. 2 is a view similar to FIG. 1 but showing the device in expanded or open condition.

FIG. 3 is a view from the underside, showing the device applied to the penis.

FIG. 4 is a view of the device, in expanded condition, in a position in a step of applying it, shown from the top.

FIG. 5 is a side view of the device.

FIG. 6 is a exploded view showing the elements making up the device.

FIG. 7 is a view taken at Line 7—7 of FIG. 1.

FIG. 8 is a perspective view of the joint, which constitutes one of the elements of the device.

FIG. 9 is a view taken in the direction of the arrow 9 of FIG. 8.

FIG. 10 is view of the support ring.

FIG. 11 is a view showing several sizes of support rings.

DETAILED DESCRIPTION OF THE DRAWINGS

FIG. 1 shows the device in its entirety, indicated at 16, which is made up of the following parts, namely a frame 18, a support ring 20, a retainer 22, and a joint 24.

The device 16 is elongated, having an inner end, or proximate end 26, and an outer end, or distal end 28.

The frame 18 is in the form of a thin filament, or element 30, which is round or roundish in cross-section. This filament is preferably made up (FIG. 7) of a central core 30, for example of metal wire, with a coating 32 of plastic or rubber material, or other materials, bonded thereto. However, it is not limited to any particular materials.

The filament 30 is bent at a mid-portion to form a support loop 34, forming nearly, but less than, a circle, and from the circumferential ends of this loop, lead support rods at 36, which are straight, parallel, and spaced apart a short distance as will be referred to hereinbelow.

The support ring 20, as shown in FIG. 10 includes a major portion 38 of circular shape, and a small or minor portion 40 that is straight, on a tangent to a base circle concentric with the circular portion 38. Preferably both the portions 38, 40 are circular in cross-section, the portion 38 being of greater diameter, and the portion 40 of lesser diameter. The support ring 20 is detachably mounted in the joint 24 as described below.

The retainer 22 is shown in enlarged detail in FIG. 7. It is preferably of plastic material being relatively rigid, but having a small degree of flexibility. It is provided with a pair of spaced holes 42 for receiving the support rods 36, and dimensioned to enable sliding of the retainer 22 along the rods, but with sufficient friction to hold it at a set position. The retainer may be provided with a slot or space 44 (FIG. 7) to facilitate providing the desired friction with the support bars. These holes are spaced apart, resulting in the support bars 36 also being spaced apart, at a suitable distance, as referred to hereinbelow.

The joint 24 is shown in large scale in FIGS. 8 and 9. It is generally in the form of a block, having spaced jaws 46, and opening at one side as at 48. One of the jaws has a rib 50 to be referred to again. The joint being of plastic material, possesses a certain degree of flexibility, and in connecting the support ring 38 in the joint, the minor portion 40 of the ring is snapped through the slot, into the hole 52 at the rear end of the slot, and the rib 50 yieldingly holds it in the hole. The ring 20 is thus detachably mounted in the joint 24, and it is swingable about the axis 54, as shown in FIG. 10, which passes through the minor portion 40 and the hole 52. This ring 20 is swingable throughout nearly a full range, engagable with the support rods 36 on opposite sides, but in use it would assume a position indicated in FIG. 5.

The joint 24 is secured to the support rods 36 by means of extending the free ends of the support rods through holes 56 in the joint, which extend into the main hole 52. A locking pin 58 is driven into a transverse hole 60 at a position that it engages the ends of the support rods 36, and actually penetrates through the coating on the support rods, as shown in FIG. 9, thus firmly holding the joint on the support rods.

The support loop 34 as noted above, is disposed at a suitable oblique angle 62 to the support rods 36. The support ring 20 is pre-dimensioned according to an estimated comfortable size, but to accommodate different situations, the device may be provided with a set of, for example three, such rings, (FIG. 11) 20a, 20b, 20c, each with a minor portion 40 and a major portion 38. The device may be made selectively in any of various lengths according to an estimated desire, and the length of the device may not always correspond with a diameter of the support ring, and therefore supplying several support rings of different diameters with a single length frame is found expeditious.

In applying the device to the penis, the support ring 20 may be applied first, separate from the frame, but an alternate method may be utilized as referred to below.

Then as the next step, the frame is manipulated, and it will be recalled that the free ends of the support rods 36 are held connected in the joint 24. In this step, the retainer 22 is positioned under and toward the inner end of the penis, as indicated in FIG. 2. Then the outer ends of the support rods are spread, as shown in that figure, this also spreading the circumferential ends of the support loop 34. This leaves a space 64 at the outer end of substantial width. In the next step, the front ends of the support rod 36 are together positioned under the penis and moved longitudinally inward with the glans of the penis entering through the support loop which is spread or opened to substantial width to enable this step without in any way rubbing the glans. After the frame is thus moved inward to the desired position, the outer end 28 is released, and the support loop retracts and engages around the penis. As shown in the drawings, the device is shaped well to the individual elements of the penis, the glans shown as 66 terminates inwardly in a ridge 68 leaving a groove 70 inwardly thereof. Then the retainer 22 is slid forwardly or outwardly along the support rods to a position closely adjacent the front end 28 (FIG. 3). This movement draws the outer or front ends of the support rods 36, and the adjacent elements of the support loop 34, inwardly toward each other, with the corresponding portions of the support loop 34 entering into the groove 70 nearly entirely around the penis. After that step, the support ring 20 is manipulated so that the minor portion 40 is snapped through the opening 48 in the joint 24, which holds the ring 20 in place in normal use.

The overall device is dimensioned longitudinally, as determined by the length of the support rods. When it is in position, the support ring 20 and the joint 24 engage against the pubis, and limit movement of the device longitudinally inwardly. In such position, the support ring 20 fits the penis according to the size thereof, and assumes a position angled forwardly, as indicated in FIG. 5, and shown also in FIG. 3.

The support rods 36 although flexible transversely, are rigid longitudinally, and bear on the pubis and the glans 66. Also, the support ring 20 is embedded in the pubic hair, and substantially hidden, and the support loop 34 is substantially hidden by the ridge 68 of the glans.

It is within the broad scope of the invention to apply the device by first fitting the frame 18 to the penis and then, in the case of a big support ring 20, sliding the ring 20 over the penis and over the frame 18, and then connecting it to the joint 24.

The structure of the device including the support loop 34, the support rods 36, and the support ring 20, form a closed frame of force vectors in reacting against the pubis in supporting the penis in an erected position.

The support ring 20 may be made of rubber-like material to enable limited stretching thereof to accommodate changes in penis length in full erection, and provide even distribution of tension between the glans and root of the penis on the erect penis, and also to provide additional compression of the dorsal vein on the top of the penis root and increase erection.

It would be thus observed that the overall device is of minimum size, or massiveness, so as not to hinder any pleasurable actuation. The support loop 34 is smaller than the outermost diameter of the glans and is thus almost entirely hidden in the groove 70. The groove 70 does not continue completely to the underside, but on the underside, the only portions exposed are the support rods 36 and the retainer 22. These individual elements are extremely small and it is found that in use, they do not hinder actuation, and in fact, it is also found at least in the great majority of cases that they cannot even be felt by either of the partners. In this step in the relations, the device is almost hidden, and does not detract from any desired psychological condition.

The device is easily and quickly put in place, and removed therefrom. Another great advantage is that it is hygienic, and easy to maintain in a clean condition.

We claim:

1. An external penile support device, comprising,
a frame having an inner end and an outer end and including a pair of support rods, a support loop at its outer end and a support ring at its inner end, the frame adapted to be fitted to the penis with the support bars lying under and engaging the penis and the support loop and the support ring receiving and substantially encircling the penis, the device including a joint connecting the support ring and the support rods, and a retainer controlling the spacing between the support rods, the device, except for said joint and said retainer, essentially consisting only of filament elements without any additional elements or protuberances thereon, the support loop and the support ring constituting the sole means for retaining the frame on the penis.

2. A device according to claim 1 wherein, the connector and retainer are constituted by plastic material.

3. An external penile support device, of elongated shape and having an inner end and an outer end, said device comprising, a frame made up solely of a single elongated filament, the filament being bent at a midpoint to form a support loop and support rods leading from the circumferential ends of the support loop in side-by-side relation, and having free ends adjacent each other, the support rods being rigid longitudinally, but flexible laterally toward and from each other, the frame having an outer end formed by the support loop, and an inner end formed by the free ends of the support rods, the device including,
(a) a joint detachably mounted on the free ends of the support rods,
(b) a support ring, circumferentially continuous, detachably mounted on the joint, swingable on an axis transverse to the support rods and in the direction of the side-by-side positioning of the support rods,
(c) a rigid retainer slidably mounted on the support rods for controlling the transverse spacing of the support rods.

4. A device according to claim 3 wherein, at all positions of the retainer along the support rods, the retainer retains the support rods at their outer ends spaced apart transversely from each other.

5. A device according to claim 3 wherein, the rigid retainer is made up of a circumferentially continuous band, having transversely spaced holes receiving the support rods, and dimensioned for engaging the support rods with such sliding/frictional relationship to hold the retainer longitudinally at a set position.

6. A device according to claim 3 wherein, a locking pin is mounted in the joint in friction engagement with the surrounding material of, and in friction engagement with, the support rods, for securing the joint on the support rods.

7. A device according to claim 1 wherein, the joint is made of material generally rigid but with a limited amount of flexibility, and includes a pair of jaws flexible toward and from each other, and the support ring is detachably fitted between the jaws for mounting the ring on the joint.

8. A device according to claim 7 wherein, the jaws on the joint are straight transversely of the support rods, the support ring is circumferentially continuous, having a major segment circular in shape and a small segment of lesser thickness than the major position and straight in direction tangent to a base circle concentric with the ring, the small segment and the spacing between the jaws being so relatively dimensioned as to enable the small segment to be snapped between the jaws into the joint, and the ring, when so mounted on the joint, being swingable on an axis extending through the small segment and correspondingly through the joint.

9. A device according to claim 7 wherein, the support ring at its top engages the top surface of the penis.

10. A device according to claim 8 and including, a plurality of support rings of different diameters individually and selectively detachably mountable on the joint of the same device, for respectively receiving the penis of the user according to size, the rings being of difference respective diameters, and each of said rings including a minor portion and a major portion.

11. A device according to claim 3 wherein, the filament of the frame is flexible transversely, the retainer is slidable on the support rods essentially the full length of the support rods, the joint holds the free ends of the support rods at a fixed spacing, and when the retainer is positioned at the inner ends of the support rods, the support rods, outwardly of the retainer, due to their flexibility, and the corresponding side portions of the support loop, are spreadable apart to provide sufficient space therebetween to enable fitting the frame over the penis in transverse direction for applying the device to the penis.

12. A plurality of penile support devices, of elongated shape and each having an inner and an outer end, each device comprising, a frame made up solely of a single elongated filament, the filament being bent at a midpoint to form a support loop and support rods leading from the circumferential ends of the support loop in side-by-side relation, and having free ends adjacent each other, the support rods being rigid longitudinally, but flexible laterally toward and from each other, the frame having an outer end formed by the support loop, and an inner end formed by the free ends of the support rods, the device including,
(a) a joint detachably mounted on the free ends of the support rods.
(b) a support ring, circumferentially continuous, detachably mounted on the joint, on an axis transverse to the support rods and in the direction of the side-by-side positioning of the support rods,
(c) a rigid retainer slidably mounted on the support rods for controlling the transverse spacing of the support rods, and said devices being of different lengths, whereby to enable a user to select a device of such plurality according to the predetermined length, to provide for the inner end of the frame to engage the pubis of the user, and the support rods to extend along and underlay the penis, and enable the support ring to extend forwardly at an oblique angle in direction longitudinally of the pieces.

* * * * *